United States Patent

Achhammer et al.

[11] Patent Number: 6,030,505
[45] Date of Patent: Feb. 29, 2000

[54] PROCESS FOR THE CONTINUOUS PREPARATION OF PURE 5-FORMYL VALERIC ACID ESTERS

[75] Inventors: Günther Achhammer, Mannheim; Michael Röper, Wachenheim, both of Germany

[73] Assignee: BASF Aktiengesellschaft, Ludwigshafen, Germany

[21] Appl. No.: 09/011,096

[22] PCT Filed: Jul. 26, 1996

[86] PCT No.: PCT/EP96/03290

§ 371 Date: Jan. 27, 1998

§ 102(e) Date: Jan. 27, 1998

[87] PCT Pub. No.: WO97/06126

PCT Pub. Date: Feb. 20, 1997

[30] Foreign Application Priority Data

Aug. 9, 1995 [DE] Germany .......................... 195 29 239

[51] Int. Cl.[7] .............................. B01D 3/34; C07C 67/54; C07C 69/716
[52] U.S. Cl. ................................ 203/49; 203/73; 203/80; 560/177; 560/218
[58] Field of Search ................................ 203/73, 80, 91, 203/49; 560/177, 218

[56] References Cited

U.S. PATENT DOCUMENTS

| | | | |
|---|---|---|---|
| 4,931,590 | 6/1990 | Kummer et al. | 560/177 |
| 4,950,429 | 8/1990 | Vagt et al. | 560/175 |
| 5,003,102 | 3/1991 | Bertleff et al. | 560/177 |

FOREIGN PATENT DOCUMENTS

| | | |
|---|---|---|
| 125 567 | 11/1984 | European Pat. Off. . |
| 295 551 | 12/1988 | European Pat. Off. . |
| 295 554 | 12/1988 | European Pat. Off. . |
| 556 681 | 8/1993 | European Pat. Off. . |
| 94/26688 | 11/1994 | WIPO . |

OTHER PUBLICATIONS

R. H. Perry, et al., Perry's Chem. Eng. Handbook, 6th Ed., 1984, Chapter 13, p. 17, Fig. 13–14.

*Primary Examiner*—Virginia Manoharan
*Attorney, Agent, or Firm*—Keil & Weinkauf

[57] ABSTRACT

5-Formylvaleric esters are prepared in a yield of not less than 90% by distillation of a formylvaleric ester mixture of 5-formylvaleric ester and either 3- or 4-formylvaleric ester or a mixture of 3- and 4-formylvaleric esters, where the ester radicals of the respective formylvaleric esters are identical, wherein the 3- or 4-formylvaleric ester or a mixture thereof is separated from the 5-formylvaleric ester in a distillation column at a pressure in the range from 2 to 100 mbar and a temperature of not above 150° C. (measured as the temperature at the bottom of the column) and the esters used are the corresponding methyl or ethyl esters, where the purity of the 5-formylvaleric ester is not less than 98% and, as impurity, 4-formylvaleric ester is present in an amount of not more than 100 ppm.

2 Claims, No Drawings

PROCESS FOR THE CONTINUOUS PREPARATION OF PURE 5-FORMYL VALERIC ACID ESTERS

This the National Phase application of International application PCT/EP 96/03290 which has an international filing date of Jul. 26, 1996.

The present invention relates to a process for preparing 5-formylvaleric esters in a yield of not less than 90% by distillation of a formylvaleric ester mixture of 5-formylvaleric ester and either 3- or 4-formylvaleric ester or a mixture of 3- and 4-formylvaleric esters, where the ester radicals of the respective formylvaleric esters are identical.

5-Formylvaleric esters ("5-FVE") are important intermediates in the preparation of adipic acid and caprolactam, and therefore for the preparation of polyamide-6,6 and polycaprolactam. 5-FVE is generally obtained by hydroformylation of 4-pentenoic esters in admixture with the isomeric 3- and 4-formylvaleric esters. 4-Pentenoic esters are in turn generally obtainable by isomerization of 3-pentenoic esters which are themselves obtainable by carbonylation of butadiene. For the preparation of adipic acid and caprolactam from 5-FVE it is essential that the 5-FVE is of high purity. In particular, the corresponding isomeric compounds, particularly 4-formylvaleric esters (4-FVE), cause interference in the preparation of caprolactam via the 6-aminocaproic esters, since, according to previous observations, the properties of the caprolactam such as the UV index and the fiber quality, for example expressed by the fiber length, of polycaprolactam are impaired if the 5-FVEs are not of sufficient purity.

The differences in the boiling points of the isomeric formylvaleric esters at atmospheric pressure are in the range from 2 to 5° C. for the $C_1$–$C_2$-alkyl esters. Thus, for example, the boiling point difference between the corresponding methyl formyl valerates (5-FVE: 221.2° C.; 4-FVE: 223.6° C.) is only 2.4° C. This makes separation of the 5-FVE from its isomeric 3- and 4-formylvaleric esters by distillation at atmospheric pressure unsuitable for an industrial scale.

If the boiling point difference of two given homologous or isomeric compounds at a pressure p1 is bd1, and the boiling point difference of the same compounds at a pressure p2, where p2<p1, is bd2, then bd2<bd1 (see R. H. Perry, D. Green, Perry's Chemical Engineers Handbook, 6th Ed., 1984, Chapter 13, p. 17, FIG. 13–14). Distillation under reduced pressure is therefore also unsuitable, since the boiling point differences also become smaller as the pressure becomes less.

In the example given in EP-B 295 551, under b), a formylvaleric ester mixture is separated by fractional distillation without any indication of experimental parameters such as pressure and temperature. There is no information about the content of 4-formylvaleric ester in the 5-FVE fraction, although it can be presumed that it was significantly greater than 100 ppm (based on the amount of 5-FVE): in the fractional distillation in step b) of the example given in EP-B 295551 over 3% by weight (10 g) of a residue were formed. Such a high proportion of residue can only be explained by the thermal decomposition of the formylvaleric esters during the distillation. This in turn enables it to be concluded that the distillation was carried out at relatively high temperatures and finally at atmospheric pressure or only slightly reduced pressure. Under such conditions, the formylvaleric esters can, as indicated above, be separated only with difficulty owing to the low boiling point difference. The 5-FVE fraction therefore contained, with a probability verging on certainty, significant amounts, ie. greater than 100 ppm, of the isomeric formylvaleric esters, in particular the 4-formylvaleric ester, since this is generally present in greater amounts than the corresponding compound substituted in the 3 position. A further indication of the poor separation of the isomeric compounds is the composition of the second fraction: this contained 2% by weight of methyl 5-formylvalerate, 70% by weight of methyl 4-formylvalerate and 28% by weight of methyl 3-formylvalerate.

Further disadvantages of the fractional distillation of the formylvaleric esters described in EP-B 295 551 are the loss of the desired product 5-FVE (2% by weight in the second fraction) and the formation of a residue.

It is an object of the present invention to provide a process for the effective and efficient separation of 5-FVE from a mixture with its isomeric 3- and 4-formylvaleric esters in a purity of greater than 98% and a content of 4-formylvaleric ester of not greater than 100 ppm (based on the amount of 5-FVE). Furthermore, it is also an object of the present invention to provide a process which allows the 5-FVE to be isolated in the abovementioned purity from the reaction mixture obtained in the hydroformylation of 4-pentenoic ester. In addition, the yield of 5-FVE should be not less than 90%.

We have found that this object is achieved by an improved process for preparing 5-formylvaleric esters in a yield of not less than 90% by distillation of a formylvaleric ester mixture of 5-formylvaleric ester and either 3- or 4-formylvaleric ester or a mixture of 3- and 4-formylvaleric esters, where the ester radicals of the respective formylvaleric esters are identical, which comprises separating the 3- or 4-formylvaleric ester or a mixture thereof from the 5-formylvaleric ester in a distillation column at a pressure in the range from 2 to 100 mbar and a temperature of not above 150 ° C. (measured as the temperature at the bottom of the column) and using as esters the corresponding methyl or ethyl esters, where the purity of the 5-formylvaleric ester is not less than 98% and, as impurity, 4-formylvaleric ester is present in an amount of not more than 100 ppm.

In view of the fact that the abovementioned prior art and general technical knowledge not only do not suggest a separation by distillation, in particular under reduced pressure, but point away from such a process, it was surprising that in the search for a solution to the present problem it was found that a pressure reduction does not decrease, but rather increases, the boiling point differences of the isomeric formylvaleric esters, in particular the $C_1$–$C_2$-alkyl compounds.

Furthermore, a process has been found wherein the formylvaleric ester mixture used is replaced by a mixture obtainable from the output of a hydroformylation of 4-pentenoic ester or a mixture of 2-, 3- and/or 4-pentenoic esters, comprising (a) a formylvaleric ester mixture,
(b) the pentenoic ester(s) used,
(c) valeric ester,
(d) high boilers and
(e) low boilers and (1) low boilers, the pentenoic ester(s) and valeric ester are first separated off by distillation via the top in a first distillation column (low boiler column) at a pressure in the range from 10 to 300 mbar and bottom temperatures in the range of not greater than 150° C.,
(2) the remaining bottoms are fed to a further distillation column (isomer column) and 3- and/or 4-formylvaleric esters are separated off via the top at a pressure in the range from 2 to 100 mbar and bottom temperatures in the range of not greater than 150° C. and (3) the remaining bottoms are fed to a further distillation column (pure column) and 5-formylvaleric ester is separated off via the top at a pressure in the range from 1 to 20 mbar and bottom temperatures in the range of not greater than 150° C.

Formylvaleric ester mixtures comprising 5-formylvaleric ester and 5 either 3- or 4-formylvaleric ester or a mixture of 3- and 4-formylvaleric esters, where the ester radicals of the respective formylvaleric esters are identical, are generally obtained by catalytic hydroformylation of the corresponding 4-pentenoic ester or the corresponding 3-pentenoic ester which is isomerized in a first reaction step to form the 2- and 4-pentenoic esters, so as to give a mixture of 2-, 3- and 4-pentenoic esters, where, in a subsequent reaction step, the 4-pentenoic ester is terminally hydroformylated with high regioselectivity.

Alternatively, the isomerization can also be carried out as a separate process step preceding the hydroformylation, with the isomerization mixture having to be at least enriched by distillation in the 4-pentenoic ester which is present in only a low concentration at equilibrium. The hydroformylation of pentenoic esters to give 5-formylvaleric esters generally requires the presence as catalyst of a metal compound of transition group VIII which is capable of forming metal carbonyl complexes under the synthesis conditions. Preference is given to cobalt or rhodium compounds which can be modified by ligands such as phosphines or phosphites. Depending on the composition of the pentenoic ester isomers, the following preferred processes have been found to be useful:

1. Cobalt catalysts

Cobalt compounds, ie. cobalt carbonyls or precursors which can be converted into cobalt carbonyls under the reaction conditions, are usually able to convert pentenoic esters, including isomer mixtures containing 2- and 3-pentenoic esters (PEs), into formylvaleric esters with a selectivity of around 95% at conversions of <70%, with the n-content being able to be up to 70% according to EP-B 295 554. Higher conversions are likewise possible, but, according to previous observations, lead to selectivity losses because of increased by-product formation.

2. Rhodium/triphenylphosphine catalysts

According to EP-B 125 567, among the pentenoic ester isomers only 4-pentenoic ester can be converted into 5-formylvaleric ester using these catalysts. Accordingly, in the hydroformylation of pentenoic ester mixtures only the 4-pentenoic esters reacted; the following steps are carried out:

a) the isomerization of the 3-PE to give mixtures of isomeric PEs and the distillative enrichment of the isomerization mixture to a 4-PE content of about 95% (described in detail in EP-B 125 567), b) the selective hydroformylation of the 4-PE to give predominantly 5-FVE (use is made of the hydroformylation catalyst rhodium/P($C_6H_5$)$_3$), and c) the distillative separation of the formylvaleric esters and return of the PEs to step a).

3. WO 94/26688 describes water-soluble rhodium/phosphine catalysts

Using these catalysts, it is likewise possible to convert, from among the pentenoic ester isomers, only the 4-pentenoic ester into 5-formylvaleric ester. Accordingly, in the hydroformylation of pentenoic ester mixtures only the 4-pentenoic ester reacts. The process comprises the same three steps specified under 2.:

a) isomerization of the 3-PE to give mixtures of isomeric PEs;
distillative enrichment of 4-PE, b) selective hydroformylation of the 4-PE to give predominantly 5-FVE; (preference is given to the water-soluble hydroformylation catalyst rhodium/P(m-$C_6H_4SO_3Na$)$_3$), c) distillative separation of the formylvaleric esters and return of the PEs to step a).

4. EP-A 556 681 describes rhodium/chelating phosphite catalysts

The hydroformylation of pentenoic esters to give 5-formylvaleric esters occurs particularly advantageously in the presence of Rh/chelating phosphite catalysts. If internal pentenoic esters are used, the isomerization of the pentenoic esters usually occurs in the same process step prior to the actual hydroformylation owing to the significantly higher reactivity of the 4-PE compared with the other isomers, this is by far preferentially hydroformylated so that 5-FVE is obtained selectively. Examples demonstrate the use of 4-, 3- and 2-PE and also a mixture of 3- and 4-PE. A regioselectivity to the 5-formylvaleric ester of up to 94% (cis/trans-3-pentenoic ester used) is obtained.

Suitable pentenoic esters are derived from alkanols having from 1 to 12 carbon atoms or cycloalkanols having from 5 to 8 carbon atoms. Particular preference is given to $C_1$–$C_{12}$-alkyl pentenoates, in particular $C_1$–$C_4$-alkyl pentenoates, eg. methyl pentenoate. Suitable compounds are, for example, 4-pentenoic esters, 3-pentenoic esters and 2-pentenoic esters, either individually or as mixtures. Examples which may be mentioned are methyl, ethyl, propyl, isopropyl, butyl, hexyl, nonyl, dodecyl, cyclopentyl or cyclohexyl esters of 2-, 3- or 4-pentenoic acid, particularly preferably the methyl and ethyl esters.

According to the present invention, a formylvaleric ester mixture of 5-formylvaleric ester and either 3- or 4-formylvaleric ester or, preferably, a mixture of 3- and 4-formylvaleric esters, where the ester radicals of the respective formylvaleric esters are identical, is distilled and the 3- or 4-formylvaleric ester or a mixture thereof is separated from the 5-formylvaleric ester in a distillation column at a pressure in the range from 2 to 100 mbar, in particular from 5 to 50 mbar, and a temperature of not above 150° C., preferably in the range from 100 to 130° C. (measured as the temperature at the bottom of the column). Methyl or ethyl esters are used according to the present invention.

A preferred starting mixture has the following composition:

from 60 to 98% by weight, in particular from 80 to 96% by weight, of methyl 5-formylvalerate, from 1 to 20% by weight, in particular from 2 to 10% by weight, of methyl 4-formylvalerate, from 1 to 20% by weight, in particular from 2 to 10% by weight, of methyl 3-formylvalerate and from 0 to 2% by weight, in particular from 0 to 1% by weight, of high boilers.

The 5-FVE remaining in the bottoms has, according to the present invention, a purity of not less than 98%, preferably not less than 98.5%, and contains the 4-formylvaleric ester in an amount of less than 100 ppm, in particular less than 80 ppm, as impurity.

The distillation apparatus used is usually a distillation column, preferably a packed column having at least 30, in particular from 35 to 50, theoretical plates. In a particularly preferred embodiment, use is made of a packing column in which the packing material has an ordered structure. Such packing materials are commercially available, for example from Sulzer under the designation DX or DY.

In a particularly preferred embodiment, the formylvaleric ester mixture used is replaced by a mixture obtainable from the output of a hydroformylation of 4-pentenoic ester or a mixture of isomeric 2-, 3- and/or 4-pentenoic esters, comprising
(a) a formylvaleric ester mixture,
(b) the pentenoic ester(s) used,
(c) valeric ester,
(d) high boilers and
(e) low boilers
and
(1) low boilers, the pentenoic ester(s) and valeric ester are first separated off by distillation via the top in a first distillation column (low boiler column) at a pressure in the range from 10 to 300 mbar, preferably from 20 to 100 mbar (measured as pressure at the top of the column), and bottom temperatures in the range of not greater than 150° C., in particular in the range from 100 to 130° C.,
(2) the remaining bottoms are fed to a further distillation column (isomer column) and 3- and/or 4-formylvaleric esters are separated off via the top at a pressure in the range from 2 to 100 mbar, in particular from 5 to 50 mbar (measured as pressure at the top of the column) and bottom temperatures in the range of not greater than 150° C., in particular in the range from 100 to 130° C., and
(3) the remaining bottoms are fed to a further distillation column (pure column) and 5-formylvaleric ester is separated off via the top at a pressure in the range from 1 to 20 mbar, in particular from 1 to 10 mbar (measured as pressure at the top of the column), and bottom temperatures in the range of not greater than 150° C., in particular in the range from 100 to 130° C.

The term low boilers refers to all compounds having boiling points lower than that of the formylvaleric ester. Correspondingly, the term high boilers encompasses all those compounds which have boiling points higher than that of 5-FVE.

The process preferred according to the present invention gives 5-FVE in a purity of at least 98%, preferably greater than 98.5%, and an amount of 4-formylvaleric ester as impurity of not greater than 100 ppm, in particular not greater than 80 ppm, based on the amount of 5-FVE.

If the formylvaleric ester mixture is prepared by means of homogeneous rhodium catalysis and the catalyst is thus still present in the reaction mixture after the hydroformylation, it is advisable to remove the catalyst before the abovementioned first distillation stage, preferably by distilling the hydroformylation product at a temperature of preferably not more than 120° C. and a pressure of generally not more than 30 mbar; the further procedure is then as described above.

A further preferred embodiment provides for the above-described process steps to be carried out in the presence of very little oxygen, preferably with exclusion of oxygen.

For this purpose, use can be made of distillation apparatuses which are welded at the contact points at which the individual parts to be connected to one another abut. Likewise, when flange connections are used, penetration of atmospheric oxygen from outside into the apparatus can be prevented or minimized by application of appropriate protective gas envelopes around the flange.

A certain proportion of oxygen can be accepted for the procedure in practice, as a rule the $O_2$ content/hour depending on the desired degree of decomposition of 5-FVE and on the duration of the distillation. The empirical equation I $$\% \text{ decomposition of 5-FVE} = (3.96 \cdot 10^{-4} \cdot a + 1.8) \cdot t \qquad \text{I}$$

where a is the $O_2$ content in ppm/h and t is the time in h,
can be used as a basis for 130° C. and 0 <t<5 h.

If, for example, the decomposition of 5-FVE is not greater than 5% in the course of 2 ½ hours, an $O_2$ content of not more than 505 ppm/h could be permitted.

The process of the present invention has the advantage over processes of the prior art that 5-FVE can be made available on an industrial scale in high purity and with a 4-formylvaleric ester content which can be disregarded for subsequent further processing, in particular for the preparation of polycaprolactam fibers.

EXAMPLES

In all the examples, the expression "ester" always refers to the methyl ester.

Example 1

120 kg of a hydroformylation product whose composition is given in the table below was worked up by distillation. The low boilers were separated off in a packed column (Sulzer CY, 10 theoretical plates) at a pressure at the top of the column of 40 mbar and a bottom temperature of 113° C., the isomer separation was carried out in a packed column (Sulzer DX, 40 theoretical plates) at a pressure at the top of the column of 12 mbar and a bottom temperature of 112.5 ° C. and the high boilers formed were separated from the 5-FVE in a thin-film evaporator superposed by a packed column (Sulzer CY, 20 theoretical plates) at a pressure at the top of the column of 4 mbar and a bottom temperature of 130° C. as bottom product. This resulted in a total 5-FVE yield of 94% (67.7 kg) based on the amount of 5-FVE in the feed to the work-up. The 5-FVE purity was 98.5%. The 4-FVE content was 80 ppm (based on 5-FVE). The yield of 3-/4-FVE isomer mixture was 99% (11.8 kg).

In the experiment carried out, the decomposition of 5-FVE by oxygen was not greater than 6% (total yield: 94%). According to the empirically determined equation I, a maximum $O_2$ concentration of 510 ppm $O_2$/h is obtained for a distillation time t of 3 h.

Example 2

Example 1 was repeated, but the pressure at the top of the isomer separation column was increased to 20 mbar, with the bottom temperature being 132° C. The total 5-FVE yield dropped to 92% of the amount of 5-FVE fed in. The purity of the 5-FVE was 98.5%, the content of 4-FVE was 80 ppm (based on 5-FVE).

Comparative Example 1

Example 1 was repeated, but the pressure at the top of the column in the high-boiler separation was increased to 8 mbar. The bottom temperature required was 158 ° C. The total 5-FVE yield dropped to 89% of the amount of 5-FVE fed in.

Comparative Example 2

100 g of 5-FVE were heated for 3 hours at 130° C. with 7 mg of oxygen per g of FVE and hour. This resulted in decomposition of 20% by weight of the 5-FVE used.

Comparative Example 2 was repeated at different residence times and an oxygen content of less than 10 ppm (based on 5-FVE):

after a residence time of 1 hour, 1% by weight of the 5-FVE had decomposed, after a residence time of 3 hours, 4% by weight of the 5-FVE had decomposed, and after a residence time of 7 hours, 8.5% by weight of the 5-FVE had decomposed.

Preparation of the hydroformylation product 637 kg of a mixture of 0.2% by weight of methyl cis-2-pentenoate, 71.5% by weight of methyl cis-3-pentenoate, 23.8% by weight of methyl trans-3-pentenoate, 0.85% by weight of methyl trans-2-pentenoate, and 3% by weight of β-picoline and about 0.6% by weight of unidentified impurities were exposed to an atmosphere of synthesis gas ($CO/H_2$ volume ratio=1:1) in a two-vessel cascade at 100° C., a pressure of 4 bar and a residence time of 5 hours in the presence of a commercial rhodium catalyst (Rh content: 120 ppm, based on the mixture). After cooling and depressurization to ambient pressure, the hydroformylation product obtained was used in the corresponding examples. The composition of the product is given in the table below.

TABLE

Composition of the hydroformylation product

| Compound | Content in the feed (in % by weight) |
|---|---|
| Low boilers | 2.96 |
| PE | 26.83 |
| 3-FVE | 4.66 |
| 4-FVE | 5.27 |
| 5-FVE | 60.04 |
| High boilers | 0.22 |

We claim:

1. A process for separating 5-formylvaleric esters in a yield of not less than 90% by distillation of a mixture, obtained from the output of a process for the hydroformylation of 4-pentenoic ester or a mixture of 3-and/or 4-pentenoic esters, comprising (a) a formylvaleric ester mixture, (b) the pentenoic ester(s) used, (c) valeric ester, (d) high boilers and (e) low boilers by distilling off the (1) low boilers, the pentenoic ester(s) used and valeric ester via the top in a first distillation column (1), low boiler column, at a pressure in the range from 10 to 300 mbar and bottom temperatures in the range of not greater than 150° C., (2) feeding the remaining bottoms from (1) to a second distillation column(2), isomer column, and separating off 3 and/or 4-formylvaleric esters via the top at a pressure in the range from 2 to 100 mbar and bottom temperatures in the range of not greater than 150° C. and (3) feeding the remaining bottoms from (2) to a third distillation column (3) and separating 5-formylvaleric ester via the top at a pressure in the range from 1 to 20 mbar and bottom temperatures in the range of not greater than 150° C. wherein the process steps are carried out at 0<t<5 h.

2. A process as claimed in claim 1, wherein the process steps are carried out in the presence of less than 10ppm of oxygen or with exclusion of oxygen.

* * * * *